United States Patent [19]

Merlen et al.

[11] 4,247,204
[45] Jan. 27, 1981

[54] METHOD AND APPARATUS FOR A WEB EDGE TRACKING FLAW DETECTION SYSTEM

[75] Inventors: Monty M. Merlen, Stamford; Frank A. Slaker, Norwalk, both of Conn.

[73] Assignee: Intec Corporation, Trumbull, Conn.

[21] Appl. No.: 16,003

[22] Filed: Feb. 26, 1979

[51] Int. Cl.³ .............................................. G01N 21/01
[52] U.S. Cl. .................................... 356/431; 250/563; 250/572; 356/237
[58] Field of Search ....................... 356/237, 238, 431; 250/557, 559, 562, 563, 572

[56] References Cited

U.S. PATENT DOCUMENTS

| | | | |
|---|---|---|---|
| 2,220,737 | 11/1940 | Jones | 250/559 |
| 3,646,353 | 2/1972 | Bhullar et al. | 356/431 |
| 3,900,265 | 8/1975 | Merlen et al. | 356/431 |
| 4,160,913 | 7/1979 | Brenholdt | 250/563 |

Primary Examiner—John K. Corbin
Assistant Examiner—Bruce Y. Arnold
Attorney, Agent, or Firm—Parmelee, Johnson, Bollinger & Bramblett

[57] ABSTRACT

A web of moving material is successively scanned by a light source, such as a laser beam, and changes of intensity of the transmitted, reflected or scattered light from the material is detected to provide an indication for discerning flaws in the web. A once per scan line digital signal from the scanner controls a voltage controlled oscillator connected in a phased locked loop which is used for controlling the generation of a precision ramp analog voltage that follows the angular scan position of the light source on the material. The light signal from the web is applied to a comparator for providing a digital pedestal signal in which the first light passing the comparator is the leading edge of the web while the last light passing during a scan line is the trailing edge or the end of the web. If no pedestal signal is present indicative of a break in the web, a synthetic maximum width pedestal signal is substituted to enable the inspection system to continue to function. The digital pedestal signal or synthetic maximum width pedestal signal and the precision ramp are applied to leading and trailing edge, position-to-voltage converters. The precision ramp voltage is sampled and held by the voltage converters which generate leading and trailing edge position analog voltage outputs. These voltage outputs are applied to a leading and trailing edge cross web, down web position tracking rate filter which is controlled by edge position tracking rate and web speed circuits. The filtered leading and trailing edge outputs are applied to margin set circuits and then are converted by voltage-to-edge, position converter circuits into digital active scan pulses that accurately define and track the active scan interval of interest where flaws are to be detected.

9 Claims, 8 Drawing Figures

METHOD AND APPARATUS FOR A WEB EDGE TRACKING FLAW DETECTION SYSTEM

BACKGROUND OF THE INVENTION

This invention relates to a flaw detection system for the detection of flaws on a moving web of material, and more particularly to a method and apparatus for such a system which tracks the lateral edge movements of the web by generating a precision ramp analog voltage precisely related to the position of the scanning beam on the web of material, sampling and holding the various levels of the precision ramp voltage at predetermined time intervals for deriving edge position outputs which are converted to digital active scan pulses which accurately follow any lateral movement of the web.

U.S. Pat. No. 3,900,265 entitled *Laser Scanner Flaw Detection System* and U.S. Pat. No. 3,980,891 entitled *Method And Apparatus For A Rotary Scanner Flaw Detection System* which are both assigned to the assignee of the present invention, disclose flaw detection systems of the general type embodied in the present invention. In the aforesaid systems, flaws are detected on the surface of the material being examined by repetitively scanning a suitable light source, such as a laser beam, across the moving web of material. The laser light is reflected, transmitted, or scattered from the material, depending upon the characteristics of the material which light is picked up by a receiver having a suitable detector, such as a photomultiplier tube. At any instant of time during the scan, the photomultiplier output varies with the reflectivity, transmissivity or scattering properties of the spot of light on the material on which the laser beam is impinging, and deviations from normal variation provides a means for indicating flaws in the material.

In the prior art systems, whether a scanning mirror utilizing a galvanometer drive or a multi-faceted mirror drum is used for scanning in accordance with the aforesaid patents, a digital signal is derived for each scan line by a photoelectric or a magnetic pick up which provides a reference mark for each scan line. This reference mark, which has been referred to as a "once-per-facet" pulse, is used to synchronize counting and timing circuits driven by a high frequency crystal oscillator to establish the active scan intervals on each scan line. The active scan digital pulses from the timing circuits have a fixed time relationship with the reference mark during each scan and as such the digital pulses generated to determine the active scan interval have angular or positional variations depending on the speeding up or slowing down of the scanning mirror. Thus, the digital pulses previously used to establish the active scan interval on the material did not bear an accurate angular or positional relationship with respect to the position of the light beam on the web during an active scan interval. Furthermore, if the web of moving material jittered or was displaced laterally as it passed under the scanning laser beam the active scan interval, as defined by the timed digital pulses, would not follow such lateral movement. Even if some means were provided for the digital pulses to track the edges, the accuracy of the system would still be limited to the resolution which could be provided by the number of digital pulses generated during an active scan interval. To improve resolution using digital timing would require counter and clocking circuits of considerably higher speeds requiring more hardware and considerably more expense.

In some applications for flaw detection systems, such as the examination of coated webs, it is desireable to be able to set margins so that the edges which are not coated are not counted as defective portions of the web. The speeding up and slowing down of the speed of the scanning motor in systems such as illustrated in the aforesaid patents would cause errors in providing such margins. Also, margin setting resolution was limited by the number of digital pulses generated per scan.

SUMMARY OF THE INVENTION

It is an object of this invention to provide a new and improved light scanning flaw detection system which tracks the edges of a moving web with substantially increased resolution.

Another object of this invention is to provide a new and improved light scanning flaw detection system with increased accuracy by accurately locating the edges of the web and tracking the angular position of the light beam on the web of material instead of using a time relationship to define the active scan interval.

A still further object of this invention is to provide a new and improved light scanning flaw detection system which provides an accurate means for setting margins on the web following web edge movements.

In carrying out this invention in one illustrative embodiment thereof a method and apparatus are provided for converting a positional digital reference pulse associated with each scan line on the material being examined into a precision analog ramp voltage which is related to the angular position of the light beam on the material. The precision analog ramp voltage is sampled and held in accordance with a pedestal signal generated from the web light signal having edge positions corresponding to the first and last light emanating from the web. The held analog leading and trailing edge position voltage outputs are further processed by an edge cross web, down web position tracking rate circuit. Margin signals are then added to the analog leading and trailing edge signals which are then converted to digital active scan pulses. The active scan pulses accurately track the edges of the web within predetermined cross web versus down web limits.

BRIEF DESCRIPTION OF THE DRAWINGS

Further aspects, objects and advantages of the present invention will be better understood from the following description taken in connection with the accompanying drawings.

DESCRIPTION OF THE PREFERRED EMBODIMENTS

Figure 1:
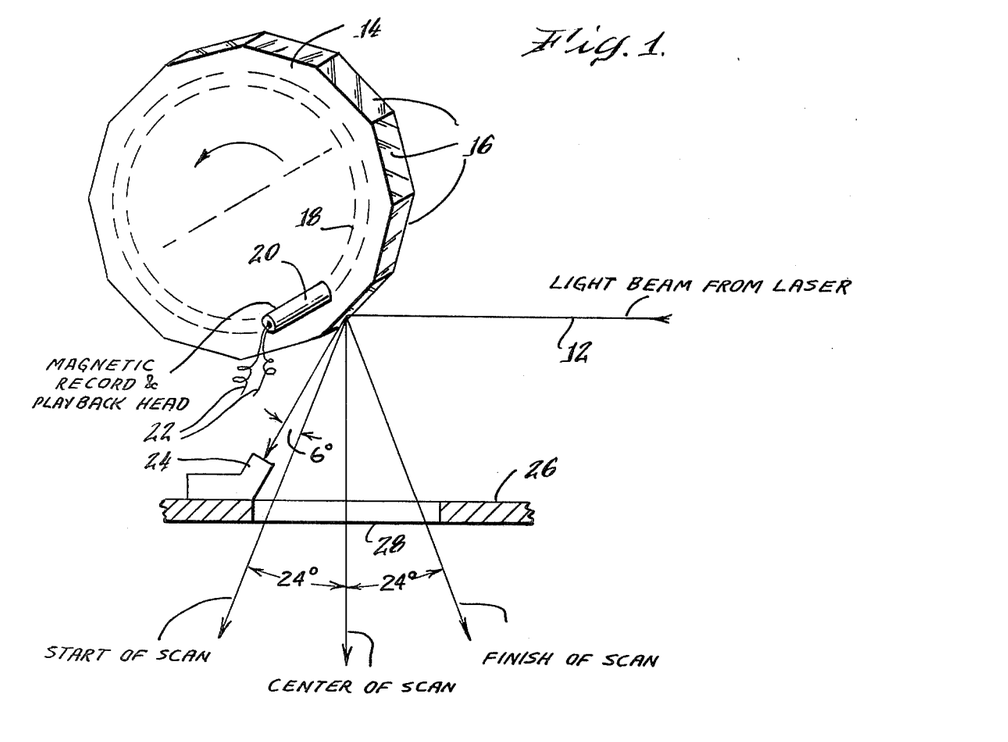
FIG. 1 schematically illustrates one form of light scanning system which may be utilized in the present invention.
Figure 2:
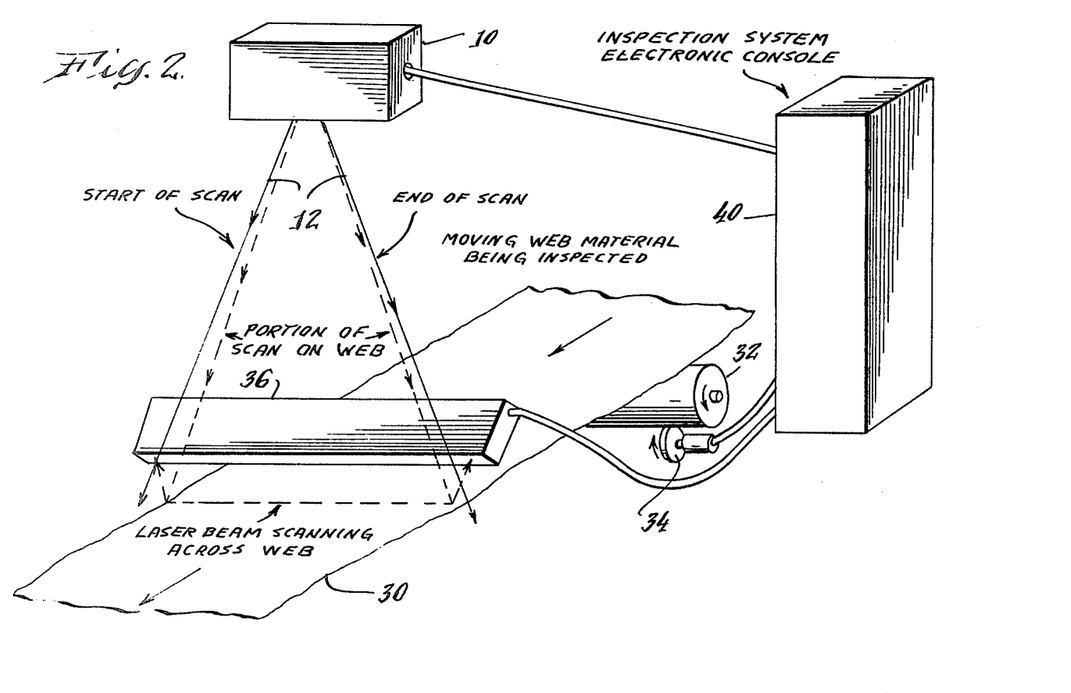
FIG. 2 illustrates one form of light scanning flaw detection system which may be utilized in connection with the present invention.

Referring now to FIGS. 1 and 2 a suitable light source, for example, a light beam 12 generated by a laser is applied to a scanner 14. The scanner 14 is a conventional multi-facet mirror surface polygon which is motor driven for rotation indicated by the direction of the arrow in FIG. 1. The rotating drum or scanner 14 has a magnetic track 18 thereon with a cooperating magnetic record and playback head 20 mounted adjacent thereto and having leads 22 which provide electrical connections to a record-playback amplifier (not shown). The cooperating magnetic record and playback head 20 and the magnetic strip 18 may be advantageously utilzed for recording "once-per-facet" signals thereon. Other control signals, for example for performing data routing functions of the type shown and described in U.S. Pat. No. 3,980,891 can be obtained from additional heads and tracks. Suitable magnetic record and playback circuitry is also described in this patent.

As shown in FIG. 1, the laser beam 12 is reflected from the mirror surface 16 and passes through a portion of the scanner housing 26 through an opening 28 therein covering a scan angle of approximately 48°. As an alternative to the recorded one per facet signal on the magnetic strip 18, a photoelectric pick-up 24 positioned on an edge of the housing 26 can be used to provide the once per facet digital signal. Therefore, the once per facet signal may be derived from other optical means such as shown in U.S. Pat. No. 3,900,265 or a magnetic pick-up may be used.

As seen in FIG. 2, the laser scanner which includes the structure of FIG. 1 is referred to generally with the reference character 10. The scanner 10 scans the light beam 12 over a moving web of material 30 which is driven in the direction of the arrow by a web drive roller 32. A rotary encoder 34 contacts the web drive roller 32 for measuring down-web increments of the moving web 30. Pulses from the encoder 34 are fed to an inspection system electronic console 40.

As will be seen in FIG. 2, the scan angle is sufficient enough so that the width of the web 30 is scanned with some overlap allowing some movement of the web 30 laterally while still permitting a complete scan of the web including its leading and trailing edges. The portion of the light beam 12 reflected from the web is picked up by a receiver 36 which includes a detector such as a photomultiplier tube and the detected signals therefrom are applied to the inspection system electronic console 40. The receiver 36 is conventional and may be of the type shown and described in U.S. Pat. No. 3,900,265. Although a reflective system is illustrated, a transmissive system may be utilized with the receiver positioned below the web as long as the receiver distinguishes the light which is actually transmitted by the web so that the edges of the web may be located.

In accordance with the present invention, an analog signal approach is taken to obtain infinite resolution, and the desired outputs of the electronics to be described are related to the position of the laser beam 12 on the material 30 rather than simply a time relationship which may be fast or slow depending upon the motor speed. Accordingly, digital signal information related to the position of the laser beam on the material is used to generate an analog voltage which is related to the angular position of the laser beam on the material, and therefore follows the angular position of the scanner. This voltage is sampled and held in accordance with the first and last light reflected from the material. The held analog signal is further processed and then converted back to a digital signal corresponding to the desired active scan interval on the web of material even when the web moves laterally.

Figure 4A:
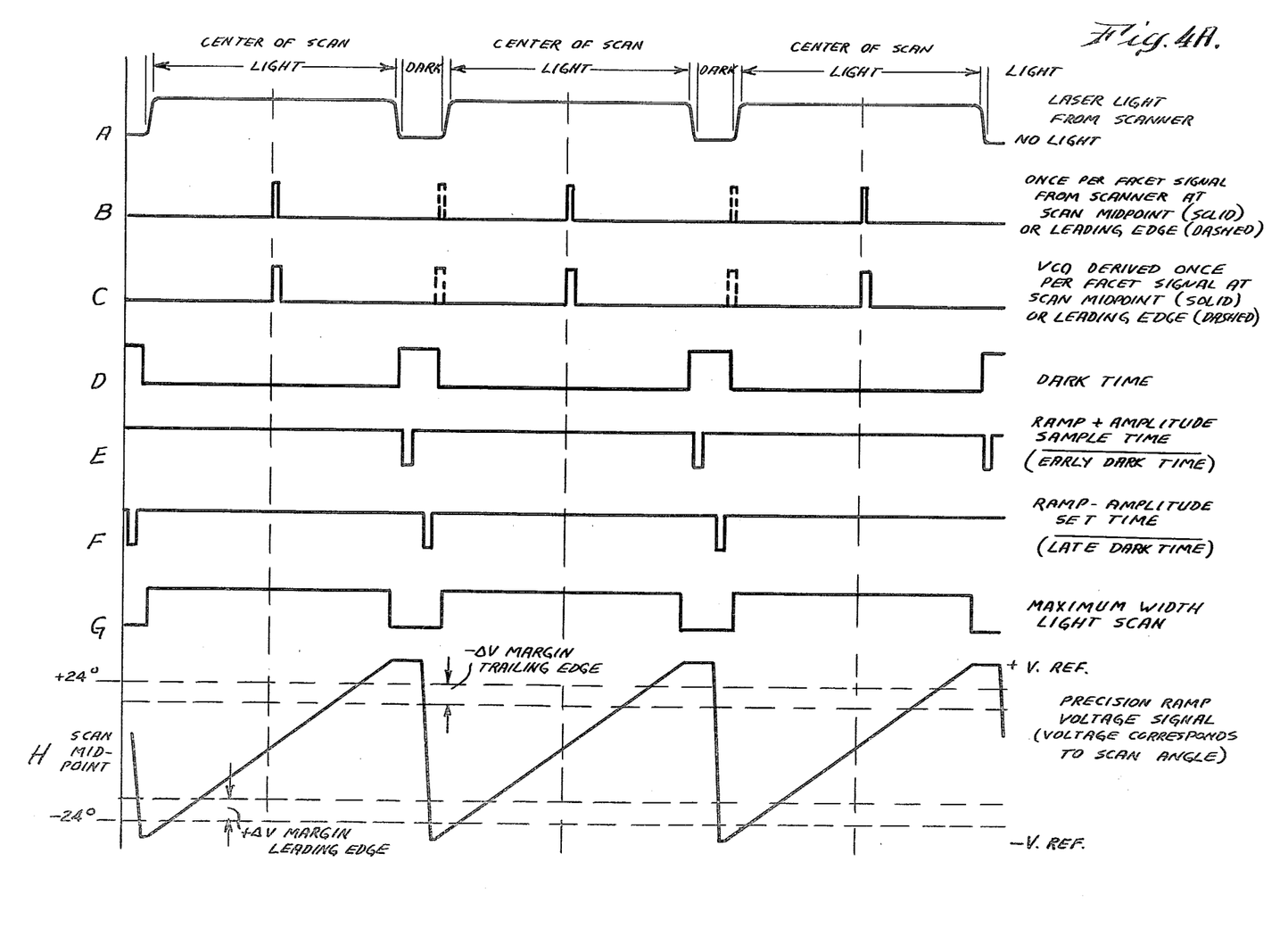
FIGS. 4A and 4B illustrate a plurality of wave forms which are generated in accordance with the present invention and which are useful in describing the operation of the edge tracking system illustrated in the block diagram of FIG. 3.

Referring briefly to FIG. 4A, wave form A illustrates a laser light emanating from the laser scanner 10 exiting from the opening 28 in housing 26. Wave form B shows the once per facet signals from the scanner 10 at the scan midpoint which are used as reference signals to delineate each scan line. The dash pulses shown on wave form B illllustrate an alternate location for the once per facet scan pulses just prior to the beginning of a scan line which would be produced by the alternative optical pick-up shown in FIG. 1. Either may be utilized as the "once-per-facet" reference signal from the scanner.

Figure 3:
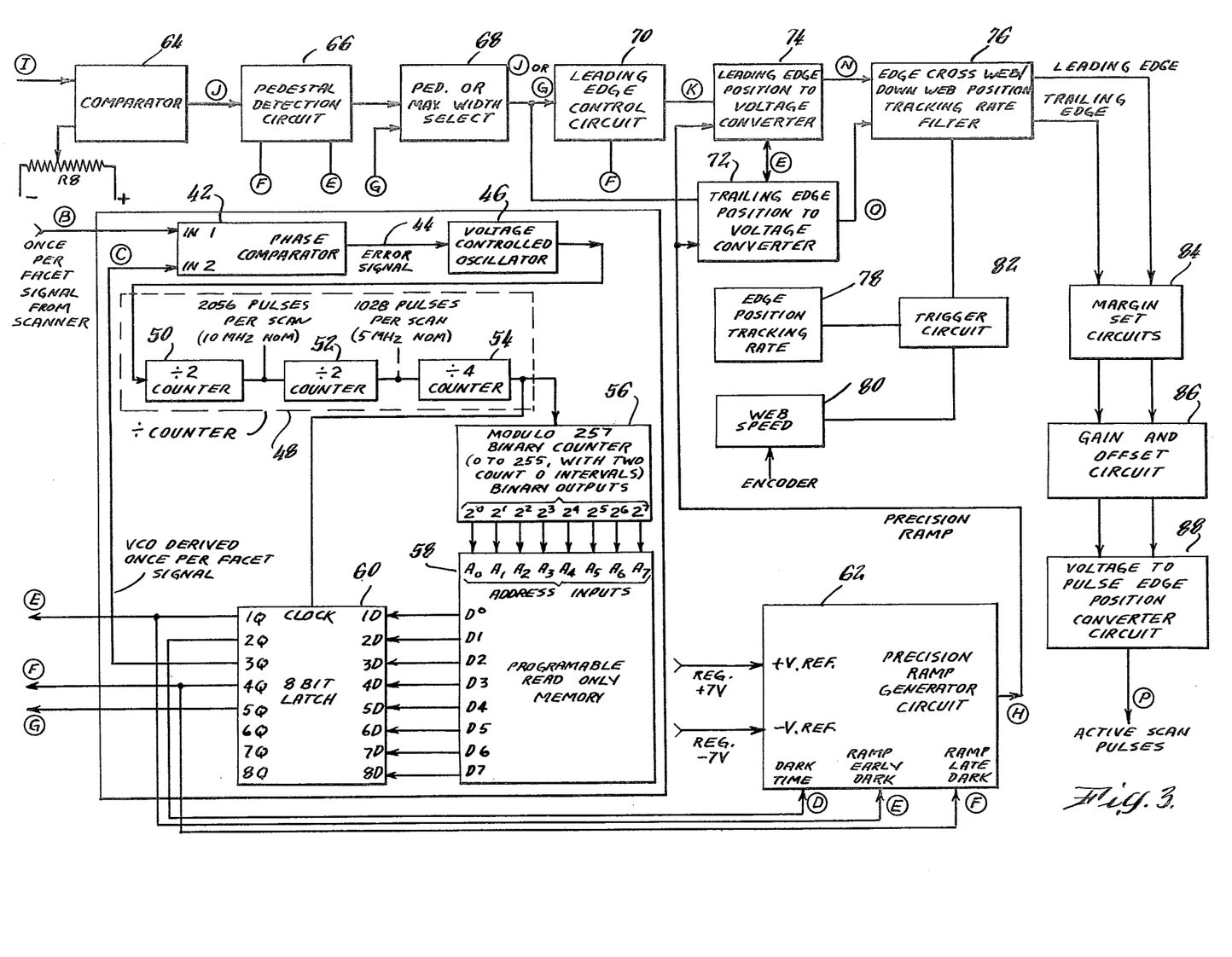
FIG. 3 is a block diagram of an illustrative embodiment of the edge tracking light scanning flaw detection system embodied in the present invention.

Referring now to the block diagram of FIG. 3, the "once-per-facet" signal from the scanner 10 wave form B is applied to one input of a phase comparator 42 which is coupled to a voltage controlled oscillator 46 which provides an output of 4,112 pulses per scan. The output of the voltage controlled oscillator 46 is applied to a divide counter 48 comprising a divide by two counter 50 whose output is 2,056 pulses per scan, a divide by two counter 52 whose output is 1,028 pulses per scan, and divide by four counter 54 whose output is comprised of 257 pulses per scan. The divide counter 48 is provided with the counters 50, 52 and 54 which supply pulses which may be used in other electronic processing in the electronic console 40. Otherwise, a divide by eight counter could be utilized.

The output of the divide counter 48 is applied to a modulo 257 binary counter having zero to 255 count intervals with two count zero intervals. Binary outputs $2^0$ through $2^7$ are respectively applied to the $A_0$ to $A_7$ address inputs of a programmable read only memory (ROM) 58. The ROM 58 functions to provide a set code related to the occurrence of pulse inputs with time. The D0 to D7 coded outputs are applied to the 1D to 8D inputs of an eight bit latch 60 which also has a clock input coupled to the output of the divide counter 48. The control signals which are fed from the ROM 58 to the eight bit latch 60 are indicative of changes in angular position of the beam 12 on each scan line.

The 3Q output of the eight bit latch 60 represents a one pulse per facet at a fixed point or angular position per facet and is illustrated in wave form C in FIG. 4A. Wave form C is applied to input 2 of the phase comparator 42 which generates an error signal 44 therefrom if the leading edge of the once per facet signal from the scanner wave form B is not in phase with the leading edge of wave form C. If wave form C is behind in phase with respect to wave form B, the error signal increases and the frequency of the voltage controlled oscillator 46 is increased. If wave forms B and C are of the same phase, the frequency of the voltage controlled oscillator remains the same. When wave form C is ahead in phase of wave form B, the error signal is lowered and the frequency of the voltage controlled oscillator decreases. Accordingly, a phase lock loop is provided that produces a "once-per-facet" output signal that locks to and follows the position of the once-per-facet signal from the scanner.

By controlling the position of the once-per-facet signal in the aforesaid phase lock loop, the various outputs from the eight bit latch 60 follow the scan position of the laser beam 12. Signals related to the scan position of the beam 12 are taken from the output of the eight bit latch 60 and applied to a precision ramp generator circuit 62 whose output wave form H is a precision analog ramp voltage which follows the angular position of the scanner 10. Wave forms E, D and F taken from the 1Q, 2Q and 4Q outputs of the eight bit latch 60 are applied to the precision ramp generator circuit 62. Wave form D is referred to as a dark time, while wave forms E and F are referred to as early dark time and late dark time, respectively, which are simply terms selected because of their relationship of the angular positions referenced to light from the scanner (wave form A) during scanning intervals.

Figures 5, 6:
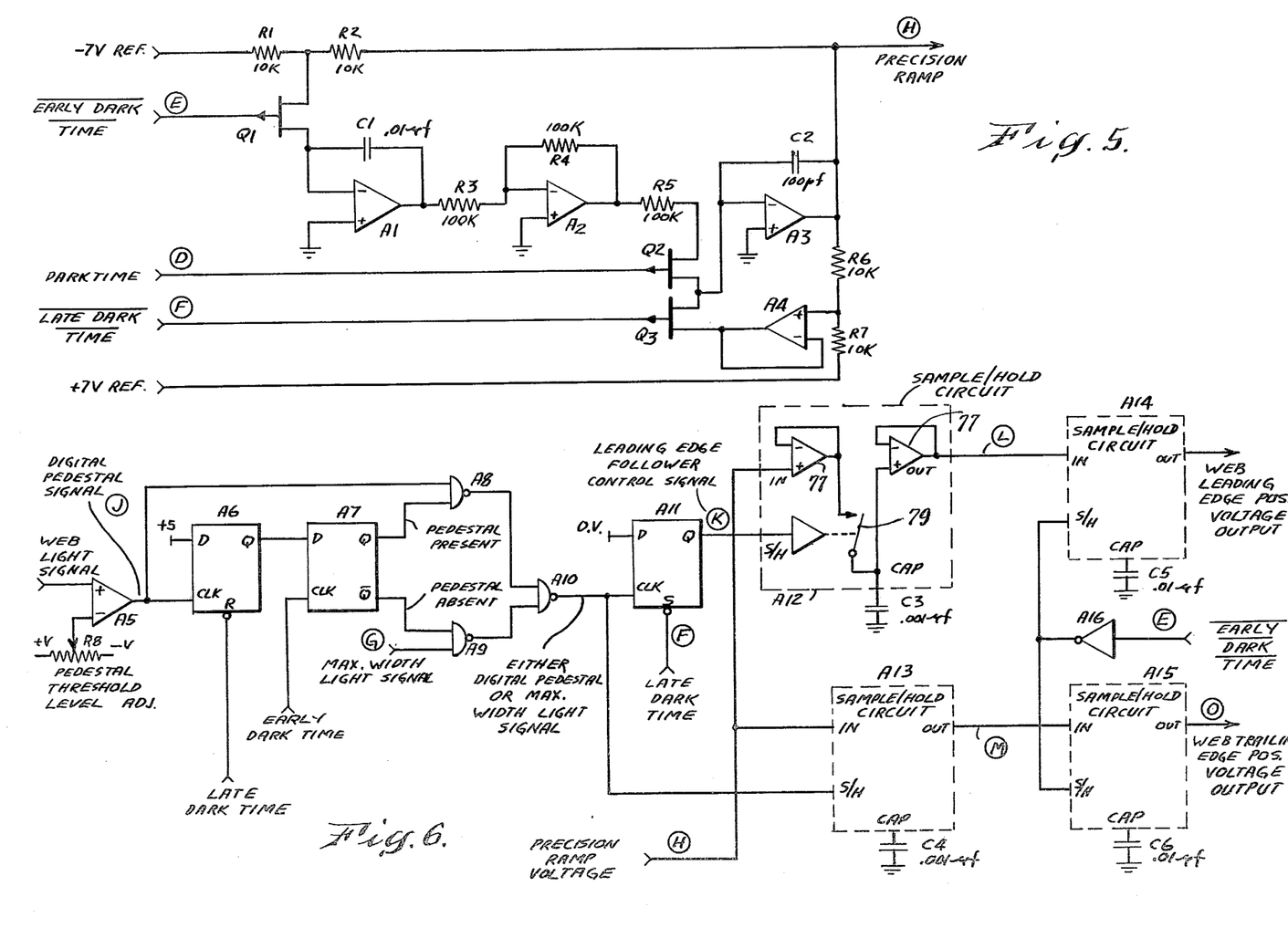
FIG. 5 is a schematic diagram of one form of precision ramp voltage generator which may be used in the present invention.
FIG. 6 is a semi-schematic block diagram which may be utilized in portions of the block diagram shown in FIG. 3 illustrating greater detail therefore.

The precision ramp generator cicuit 62 is a scan position to voltage converter circuit. FIG. 5 shows an illustrative form of precision ramp generator circuit 62 comprising a voltage divider R1 and R2 coupled through a field effect transistor (FET) switch Q1 to the minus input of an amplifier A1. The amplifier A1 is used as an integrator and has a capacitor C1 between the minus input and the output thereof. Amplifier A2 in conjunction with resistors R3 and R4 is a unity gain inverting amplifier which inverts the output of the integrator. The output of A2 is coupled through resistor R5 and FET switch Q2 to the negative input of A3 which in conjunction with C2, which is an integrator. The output of A2 is the desired precision analog ramp voltage, as illustrated on wave form H. Amplifier A4 is used as a non-inverting, unity gain amplifier of the signal present at the junction of R6 and R7. The output of A4 is coupled to the input of A3 through FET switch Q3.

Dark time wave form D, early dark time wave form E and late dark time wave form F as shown in FIG. 4A are applied to FETs Q2, Q1 and Q3, respectively in FIG. 5. Dark time wave form D which occurs during a transition between scan lines turns off Q2 when wave form D is low. Early dark time wave form E turns on Q1 which compares precision ramp wave form H with the −7 volt reference via resistors R2 and R1. If wave form H is more positive than +7 volts, the output of integrator A1 is driven more negative, and if wave form H is more negative than +7 volts, then the output of amplifier A1 will be driven positive. Accordingly, the precision ramp voltage is sampled during the wave form early dark time E at the positive end of the ramp amplitude. FET Q1 is on for a finite time, and changes at the output of A1 will be proportional to the deviation of the ramp voltage from the reference voltage of +7 during the time Q1 is on. The inverted output of integrator A1 holds constant during "light time" on wave form A and determines the ramp sweep rate or voltage change per unit time. At the end of each sweep or scan, wave form H is sampled through R1 and R2 through Q1 into A1. If the ramp amplitude is at +7 volts, no drive is provided into A1, the voltage at the output of A1 will be unchanged, and the next scan will be at the same rate. Any deviation from +7 reference level will provide a proportionate change at the output of A1 which will change the sweep rate during the next scan.

After the sample time at the top of the ramp is over, Q1 is turned off and Q3 is switched "on" by the application of the late dark time wave form F which drives the output of amplifier A3 to −7 volts via resistors R6, R7 and amplifier A4. The "on" time of switch Q3 provides the set time for the minus amplitude of the ramp. When dark time wave form D terminates, switch Q2 turns on and the precision ramp wave form H is generated, which represents the angular position of the laser beam on the moving web of material 30 as it scans across the web. In other words, the precision ramp signal voltage corresponds to the scan angle of the laser beam as it sweeps across the material being examined, and this correspondence is maintained irrespective of motor speed variations.

Figure 4B:
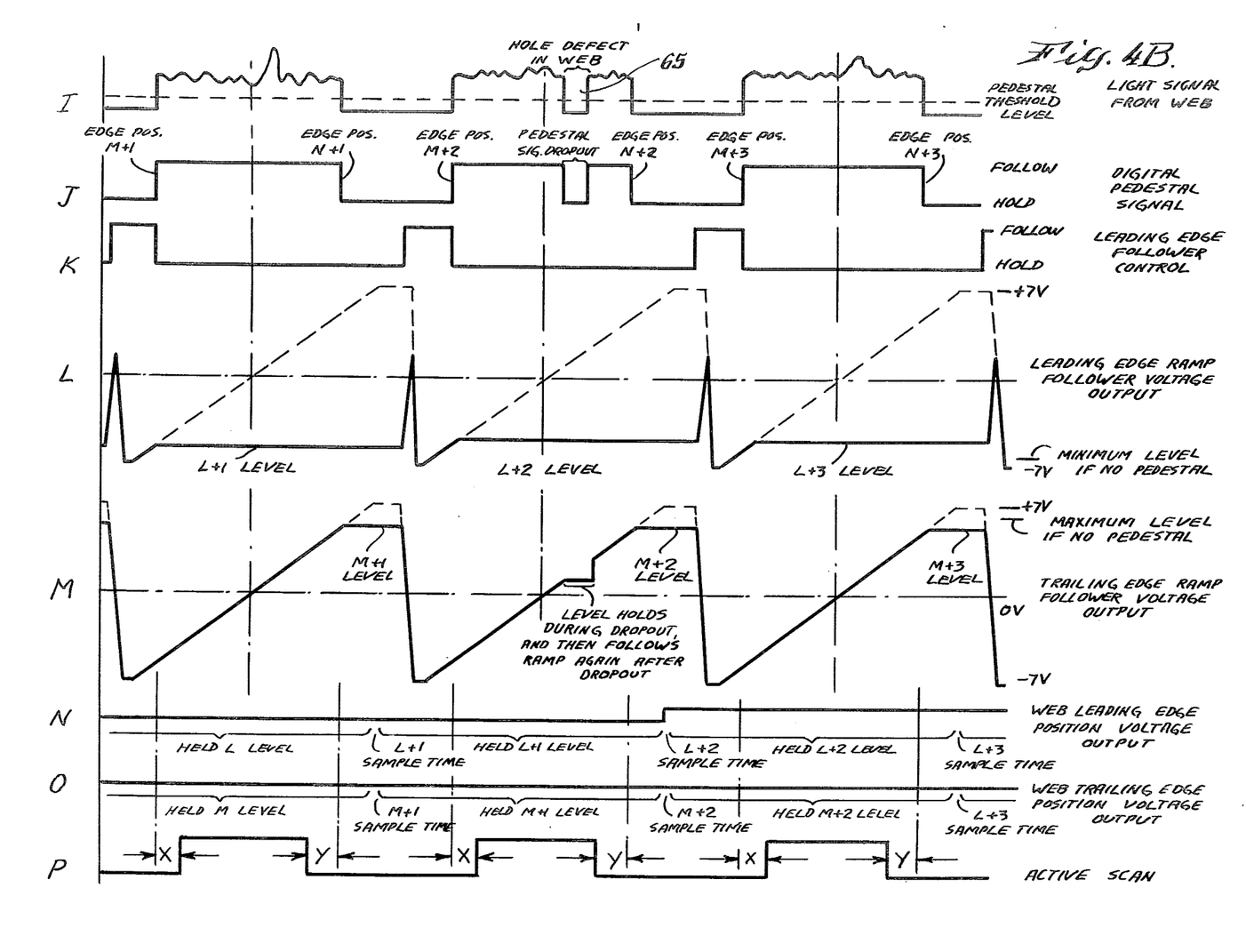

Having now derived a precision ramp voltage which follows the scan position of the laser beam on the web, the next problem is to convert the edge positions of the scan on the web utilizing the precision ramp voltage and then to reconvert the generated signals into a digital signal representative of the scan interval on the web which tracks lateral movements of the web during scanning. Referring again to the block diagram of FIG. 3, the light signal from the web which is detected by the receiver 36 is applied to a comparator 64 along with a reference signal from a potentiometer R8 which sets a pedestal threshold signal for the comparator. Signals exceeding the pedestal threshold level are transformed by the comparator 64 into a digital pedestal signal wave form J as seen on FIG. 4B. Wave form I, which is the light signal from the web, includes a defect in the web 65 which is shown processed by the various wave forms in order to indicate the effect of a loss of a portion of the pedestal signal in the comparator 64. As will be seen later, this so called drop-out has no effect.

Digital pedestal signal wave form J is applied to a pedestal detection circuit 66 along with early dark time wave form E and late dark time wave form F in order to determine if the pedestal signal is present. The output of the pedestal detection circuit 66 is applied along with a maximum width wave form G to a pedestal or maximum width select circuit 68 so that the circuit will not be disabled if a web break occurs.

The output of select circuit 68, either wave form J or G, is applied to a leading edge control circuit 70 and to a trailing edge position to voltage converter 72. The late dark time wave form F is also applied to the leading edge control circuit 70 whose output wave form K is applied to a leading edge position to voltage converter 74. The precision ramp voltage wave form H is applied to both voltage converters 72 and 74 along with the early dark time wave form E. Converter 74 generates the web leading edge position output voltage wave form N while the converter 72 provides a web trailing edge position voltage output wave form O.

Referring now to FIG. 6, comparator 64 may be in the form of a comparator amplifier A5 and the pedestal detection circuit 66 comprises a pair of flip-flops A6 and A7 with the output of comparator A5 being applied to the clock input of flip-flop A6 with the Q output thereof being applied to the D input of flip-flop A7. Flip-flop A6 is reset by late dark time wave form F while the clock input of flip-flop A7 has the early dark time wave form E applied thereto. If a pedestal crossing occurs, producing a pedestal signal J, the Q output of A7 will be high. If the pedestal is not present, the Q output will be low with the $\overline{Q}$ output being high. The pedestal or maximum width select circuit 68 is comprised of NAND-gate A8 to which wave form J and the Q output of Q7 are applied; NAND-gate A9 to which the $\overline{Q}$ output and the maximum width signal G are applied; and NAND-gate A10 which provides an output corresponding either to the digital pedestal signal J or the maximum width light signal G.

The leading edge control circuit 70 may be in the form of a flip-flop circuit A11 having the clock input applied from the output of NAND-gate A10 and the late dark time wave form F being fed to the set input S. The leading edge follower control signal wave form K which appears at the Q output of the flip-flop A11 goes high in coincidence with the occurrence of the late dark time signal F and will go low in coincidence with the leading edge of the pedestal wave form J.

The leading edge position to voltage converter 74 may be in the form of sample and hold circuits A12 and A14 while the trailing edge position to voltage converter 72 is comprised of sample and hold circuits A13 and A15. The sample and hold circuits A12 through A15 are identical. Each has an FET switch driven by a level translator 79 coupled to a capacitor C3. Elements 77 comprise input and output unity gain non-inverting buffer amplifiers. The precision ramp wave form H is applied to the input buffer of A12.

When the Q output of A11 goes high during late dark time of the leading edge of the web 30, sample and hold level translator 79 closes its switch which couples capacitor C3 to the precision ramp through input buffer amplifier 77. As long as the switch stays closed, the voltage at C3 will follow the precision ramp. When wave form K goes low in coincidence with the leading edge of the pedestal wave form J, the switch opens, and the voltage at C3 is held and transferred through output buffer amplifier 77 to sample/hold circuit A14 during early dark time. Immediately following this, during late dark time, the switch 79 is again closed and the process is repeated as illustrated in wave forms L and N. As will be seen in wave form N, the leading edge position voltage output is obtained at the end of each scan just prior to the start of the next scan. The level shown at L+2 on wave form N indicates a change of edge position that occurred during the L+2 scan interval.

A similar process takes place with respect to the trailing edge. The precision ramp voltage H is applied to A13 in conjunction with pedestal wave form J driving sample/hold circuits A13 and producing ramp follower output wave form M. Wave form M is applied to the input sample/hold circuit A15 producing output wave form O.

The remainder of the block diagram of FIG. 3 comprises an edge cross-web, down web position tracking rate filter 76 which is controlled by a trigger circuit 82 fed by edge position tracking rate circuit 78 and web speed circuit 80. The leading and trailing edges from the tracking rate filter 76 are applied to margin set circuits 84 where margins are provided from the edges of the web. The margin set circuits 84 are coupled to a gain and off-set trim circuit 86 and from there to a voltage pulse edge position converter circuit 88 for converting the edge positions to digital active scan output pulses shown in wave form P.

Figure 7:
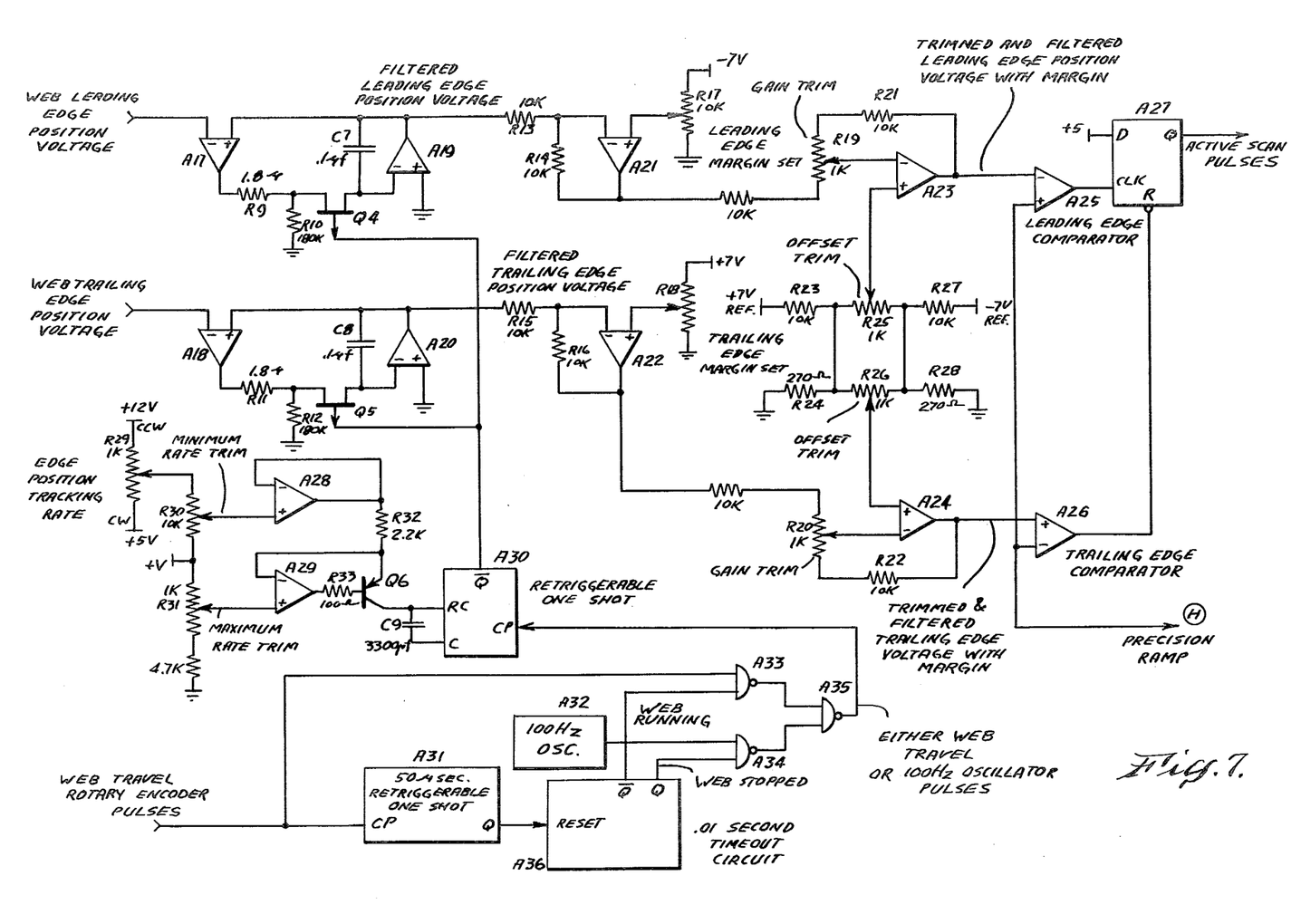
FIG. 7 is a schematic diagram which may be utilized for performing the function illustrated in portions of the block diagram of FIG. 3 in accordance with the present invention.

Circuitry for implementing the aforesaid portion of the block diagram is illustrated in FIG. 7. Referring now to FIG. 7, the web speed circuit 80 comprises a retriggerable one shot circuit A31, a timeout circuit A36, a 100Hz oscillator A32, and NAND-gates A33, A34 and A35. Web travel rotary encoder pulses are applied from the encoder 34 at the rate of one pulse per 1/20 of an inch of web travel to the 50 microsecond retirggerable one shot circuit A31 and to the NAND-gate A33. The Q output of one shot circuit A31 is coupled to a reset input of timeout circuit A36 which determines if the web is running and if so provides a Q high output to gate A33. The oscillator A32 is coupled to the gate A34 along with the Q output of "timeout" circuit A36 which, when high, indicates that the web is stopped and enables gate A34. NAND-gate A35 passes either web encoder pulses from gate A33 when the web is moving or the oscillator pulses from gate A34 when the web is stationary. Accordingly, the pulse repetition rate from the output of gate A35 is indicative of web speed when the web is moving and, if the web is stopped, the 100Hz oscillator will keep the system operative. These pulses are applied to the CP input of a retriggerable one shot circuit A30.

The edge position tracking rate circuit 78 includes a potentiometer R29 which sets the basic tracking rate. A minimum rate trim potentiometer R30 is coupled thereto along with a series connected maximum rate trim potentiometer R31. The output of potentiometer R30 is applied to an amplifier A28 through a resistor R32 and a transistor Q6 to a RC input of retriggerable one shot A30. The maximum rate trim potentiometer R31 is coupled through an amplifier A29, resistor R33 and transistor Q6 to the retriggerable one shot A30. A capacitor is coupled between the RC and C terminals of A30.

The voltage across R33 determines the current into C9. The value of current into C9 determines the duration of output pulses from A30. With R29 in a clockwise position the minimum current is set to 100 microamperes by adjusting R31. With R29 fully in a counterclockwise position the maximum current is set to 100 microamperes by adjusting R30. With these limits, R29 can be used to accurately control the current in C9.

Thus, the retriggerable one shot circuit A30 produces output pulses having duration of 10 to 100 microseconds. These pulse time durations are proportional to the tracking rate potentiometer R29 setting on the occurrence of each web travel encoder pulse. The repetition rate of the output pulses from the $\overline{Q}$ output of circuit A30 is proportional to the web speed. The $\overline{Q}$ output of A30 is applied to the edge cross-web, down web position tracking rate filter 76. This includes identical circuits for processing the web leading and trailing edge position voltages. The web leading edge circuit includes a comparator A17 coupled through a voltage divider R9 and R10 to a switch Q4 and to an amplifier A19 having a capacitor C7 connected between the input and output thereof. The web trailing edge position voltage is identical—having comparator A18, an amplifier A20, resistors R11 and R12, switch Q5 and a capacitor C8. The output of comparator A17 is either +10 volts or −10 dependent on the relative polarities at its plus and minus inputs. Q4 is on when the output of A30 is pulsing low. R9, A19 and C7 comprise an integrator. The voltage at the output of A19 which is connected to the pulse input of A17 will drive toward the web leading edge position voltage. When the plus and minus inputs of A17 are of the same level, the voltage at A19 will stop changing. The rate of change, of course, will be dependent on the pulse repetition rate from trigger A30 as well as the duration of the pulses being applied therefrom. The output of A19 will be a filtered leading edge voltage, while the output of amplifier A20 will be a filtered trailing edge voltage, both of which follow the rate of change dictated by the output of the trigger circuit A30.

With the circuits shown on FIG. 7 the maximum cross-web angular tracking rate of the web edges is adjustable by the edge position tracking rate potentiometer R29 from approximately 5° to 50° per 100 inches of web travel and will hold for web speeds ranging between 25 feet per minute and 2,500 feet per minute. At web speeds below 25 feet per minute, pulses from the oscillator A32 at a repetition rate corresponding to 25 feet per minute are automatically substituted for the encoder pulses.

If for a given application, the web edges are generally clean and well-defined and there is little web wander, then filtering may not be required. In such case, the cross-web, down-web, position tracking rate filter 76 may be dispensed with. If some filtering is desired where the web speed is relatively constant, a simple RC network may be used as filter 76.

The filtered leading and trailing edge voltages are applied to margin set circuits 84 which includes one circuit for the leading edge and one circuit for the trailing edge, both of which are identical. The leading edge margin set circuit includes resistors R13 and R14 coupled to amplifier 21 and a leading edge margin set potentiometer R17. The trailing edge margin set circuit includes resistors R15 and R16, amplifier A22 and trailing edge margin set potentiometer R18. The outputs of the margin set circuits 84 are applied to a gain and off-set trim circuit 86 which includes a gain trim potentiometer R19 coupled to an amplifier A23 with a feedback resistor R21. One of the inputs of amplifier A23 is coupled to an off-set trim potentiometer R25. The filtered gain trim potentiometer R20 is coupled to an amplifier A24. Amplifier A24 has having a feedback resistor R22 and one of its inputs coupled to a resistance network including the off-set trim potentiometer R26. The resistance network which furnishes off-set voltages to both amplifiers A23 and A24 consists of resistors R23, R24, R27, R28 as well as the off-set trim potentiometers R25 and R26. The purpose of the gain and off-set trim circuits is to adjust out all gain and off-set errors in all the sample/hold and amplifier circuits that process the analog voltages associated with edge positions. With the values indicated, setability and accuracy of better than one ten-thousandth of the total scan angle is achieved over the total edge tracking range.

The output of amplifier A23 is a trimmed and filtered leading edge position voltage with a margin while the output of A24 is a trimmed and filtered trailing edge voltage with a margin. Each output is applied to separate inputs of the voltage to pulse edge position converter circuit 88 comprising a leading edge comparator A25, a trailing edge comparator A26 and flip-flop circuit A27. The precision voltage ramp signal H is applied to inputs of both the comparators A25 and A26. The output of comparator A25 is coupled to the clock input of flip-flop circuit A27 while the output of the trailing edge comparator A26 is applied to the reset input of the flip-flop A27. The Q output of A27 consists of a digital pulse which delineates the active scan signal with the margins which have been set therein as shown in wave form P.

The present invention increases the accuracy of the entire flaw detection system by accurately locating the edges of the web and following those edges during an inspection of a web. The active scan pulses which have been generated may be utilized for controlling the interval when various discriminators detect flaws. Furthermore, the active scan pulses are automatically adjusted by the web edges which permits the examination of different width webs without setting controls to change the active scan to accommodate the different width. Also, the margins will be related to the edges regardless of the width of the web so changes in web width would not require resetting margins unless margin changes were desired.

The system of the present invention eliminates the digitizing error in locating the edges. The accuracy of prior digital systems was limited to less than one-thousandth of the total usable scan angle. The present system provides an order of magnitude improvement. Furthermore, the present system provides an accurate means for tracking margins which would be quite useful in such applications as those employing coated paper. Since the edges of the web are not coated, margins are necessary to avoid counting the edge as a defective portion of the web.

The various circuit diagrams such as FIGS. 5-7 have indicated thereon representative values for some of the components which have been found suitable for a particular application. These are merely illustrative examples and can be varied in accordance with circuit requirements.

Since other modifications and changes varied to fit particular operating requirements and environments will be apparent to those skilled in the art, the invention is not considered limited to the examples chosen for purposes of illustration and covers all changes in modifications which do not constitute departures from the true spirit and scope of this invention.

What is claimed is:

1. A method of tracking the edges of a moving web of material in a light scanning, flaw detection system, said system having a light source which is successively scanned over said moving web and a receiver for detecting light reflected, transmitted or scattered by said moving web, comprising the steps of:
   (a) generating a digital reference pulse which is synchronized to occur at a predetermined angular position during each line scanned on the web of material being examined,
   (b) generating a precision analog ramp voltage synchronized with said digital reference pulse, said precision analog ramp voltage corresponding to the angular position of said light source on said material during any given scan line,
   (c) deriving a pedestal signal from the light reflected, transmitted or scattered from said web which exceeds a predetermined amplitude,
   (d) sampling and holding said precision analog ramp voltage during the occurrence of the leading and trailing edges of said pedestal signal for providing analog voltages corresponding to the leading and trailing edge positions of said web,
   (e) adding and subtracting analog voltages representing desired margins to said analog voltages corresponding to the leading and trailing web edge positions, and
   (f) converting said leading and trailing analog edge voltages with margins to digital active scan pulses which accurately follow the light source emanating from said web.

2. The method set forth in claim 1 including the step of tracking the edges of said web within predetermined limits by adjusting the edge position tracking rate for the leading and trailing edge analog voltages after the provision of said analog voltages in said sampling and holding step.

3. The method set forth in claim 1 wherein, when no web pedestal signal is present due to the absence of said web, a maximum width pedestal signal is generated.

4. In a light scanning flaw detection system for accurately locating and tracking the edges of a moving web, said system having a light source which is successively scanned across a moving web of material and a receiver for detecting the light reflected, transmitted or scattered from said web, the improvement comprising:
  (a) means for generating a synchronized digital reference pulse for each scan line,
  (b) a precision analog voltage ramp generator,
  (c) control means coupled between said means for generating a digital reference pulse and said precision voltage ramp generator for causing the output of said precision voltage ramp generator to bear a precise angular relationship to the angular position of the light source on said web,
  (d) means for sampling and holding the output voltage of said precision voltage ramp generator when the leading and trailing edges of said web are detected by said receiver,
  (e) means for converting said levels of said precision analog voltage ramp to web leading and trailing edge position voltages, and
  (f) means for converting said leading and trailing edge position voltages to digital active scan pulses which track the lateral movements of said moving web.

5. The light scanning flaw detection system of claim 4 including means for adding and subtracting analog voltages representing desired margins to said leading and trailing position voltages, respectively.

6. The light scanning flaw detection system of claim 4 or 5 including an edge cross-web, down web tracking rate filter having said web leading and trailing edge position voltages applied thereto.

7. The light scanning flaw detection system of claim 4 or 5 wherein said control means comprises a phase comparator, a voltage controlled oscillator, a division counter, and pulse position coding means coupled in a phase locked loop.

8. The light scanning flaw detection system of claim 4 in which said means for sampling and holding the levels of said precision ramp voltage comprises a plurality of sample/hold circuits each having an input and output unity gain non-inverting buffer amplifier, a switch driven by a level translator, and a capacitor coupled between said switch and ground; wherein said precision ramp voltage is applied to the input unity gain buffer amplifiers; and wherein said leading and trailing edge position voltages are applied to said level translator driven switch for closing said switch during the occurrence of said leading and trailing edges on said web.

9. The light scanning flaw detection system of claim 4 wherein said means for converting said levels of voltage ramp includes: an edge cross-web, down web tracking rate filter; a trigger circuit having a pulse output coupled to said edge cross-web, down web tracking rate filter; a web speed circuit having web travel encoder pulses applied thereto; an edge tracking rate circuit; means for coupling said web speed circuit and said edge tracking rate circuit to said trigger circuit whereby the pulse output of said trigger circuit has a repetition rate related to the speed of said web; and a pulse duration related to the tracking rate of said edge tracking rate circuit.

* * * * *